United States Patent [19]
Flatt et al.

[11] Patent Number: 5,118,803
[45] Date of Patent: Jun. 2, 1992

[54] ZOOGLAN POLYSACCHARIDE

[75] Inventors: James H. Flatt; Timothy A. Cooper, both of Madison, Wis.

[73] Assignee: Wisconsin Alumni Research Foundation, Madison, Wis.

[21] Appl. No.: 581,818

[22] Filed: Sep. 13, 1990

[51] Int. Cl.$^5$ .............................................. C08B 37/00
[52] U.S. Cl. .................................... 536/114; 536/1.1; 536/123; 435/101
[58] Field of Search ...................... 435/101, 252.1, 1.1; 536/123, 114, 121, 127

[56] References Cited

U.S. PATENT DOCUMENTS

| | | | |
|---|---|---|---|
| 4,384,044 | 5/1983 | Kim et al. | 435/101 |
| 4,400,466 | 8/1983 | Azouley | 435/101 |
| 4,535,153 | 8/1935 | Kang et al. | 536/123 |
| 4,576,915 | 3/1986 | Harada et al. | 435/101 |
| 4,851,235 | 7/1989 | Schwartz et al. | 466/33 |
| 4,851,393 | 7/1989 | Rha et al. | 514/54 |

FOREIGN PATENT DOCUMENTS

| | | | |
|---|---|---|---|
| WO88/00948 | 2/1988 | PCT Int'l Appl. | 435/101 |
| 89/09270 | 10/1989 | PCT Int'l Appl. | 435/252.1 |
| 2139638A | 11/1984 | United Kingdom | 435/101 |
| 00952 | 2/1988 | World Int. Prop. O. | 435/101 |

OTHER PUBLICATIONS

Norberg, A. B., 1984, *Biotech and Bioeng.*, vol. 26, pp. 239-246.

Norberg, A. & Rydin, S., 1983, *Biotech. and Bioeng.*, vol. 26, pp. 265-268.

*Primary Examiner*—John W. Rollins
*Assistant Examiner*—Pamela S. Webber
*Attorney, Agent, or Firm*—Andrus, Sceales, Starke & Sawall

[57] ABSTRACT

A succinylated zooglan polysaccharide is prepared by fermentation of the microorganism *Zoogloea ramigera* 115 (ATCC No. 25935). The polysaccharide has valuable properties as a thickening, suspending, stabilizing and lubricating agent in aqueous systems. The presence of succinate in the polysaccharide enables the polysaccharide to exhibit superior thickening and metal chelating properties in commercial applications.

20 Claims, 6 Drawing Sheets

Comparison of the Steady Shear Viscosities of 1% (w/w) Solutions of Xanthan and Improved Zooglan Gums Comparison of Steady Shear Viscosity of Aqueous Solutions of 1% Improved Zooglan and Reported Zooglan Comparison of Steady Shear Viscosities of Aqueous Solutions of 0.5% Improved Zooglan and Reported Zooglan

ZOOGLAN POLYSACCHARIDE

FIELD OF THE INVENTION

The present invention is directed to zooglan polysaccharides produced from the microorganism *Zoogloea ramigera* 115 (*Z. ramigera* 115). The present invention is more specifically directed to a succinylated zooglan polysaccharide produced by *Z. ramigera* and methods of production and use.

DESCRIPTION OF THE PRIOR ART

Polysaccharides have extensive use in both food and non-food applications primarily as a result of their ability to modify the rheology, i.e., flow behavior, of aqueous systems. Examples of uses for polysaccharides include dispersants, thickeners, film forming agents, water retention agents, coagulants, colloids, lubricant/friction reducers as well as others.

Commercially valuable polysaccharides are obtained by either recovery of gums from botanical sources, e.g., seaweeds, tree exudates, and plant seeds, or microbial fermentation broths, e.g., xanthan gum from fermentation of hydrolyzed corn syrup by *Xanthomonas campestris*. The process of production and recovery from fermentation broths generally involves the following steps:
  a. aerobic fermentation of a complex medium containing a carbohydrate source, nitrogen source, trace metals, salts and vitamins;
  b. pasteurization to kill the microorganisms;
  c. addition of alkali to facilitate separation of the polysaccharide from cellular matter and the broth;
  d. addition of a short-chain, aliphatic alcohol with or without salt to precipitate the polysaccharide and cellular matter;
  e. recovery and drying of the precipitate; and
  f. milling of the precipitate to achieve the desired polysaccharide texture and solubilization properties.

Microbial polysaccharides which possess these characteristics are well known and described in the prior art. Examples include the following patents:

U.S. Pat. No. 4,384,044 to Kim et al. discloses a design for a bioreactor for the generic production of microbial polysaccharides from microorganisms supported on a porous, inner support. Examples of microorganisms include *Rhizobium meliloti*.

U.S. Pat. No. 4,851,235 to Schwartz et al. discloses the production of food and cosmetic grade emulsifying agents by fermenting whey with a microorganism (*Candida lipolytica*). Whey is disclosed as an economical source of fermentable substrates.

U.S. Pat. No. 4,400,466 to Azouley is directed to a bioreactor system for the continuous production of a Rhizobium microorganism to produce a thickening agent.

U.S. Pat. No. 4,576,915 to Harada et al. is directed to the production of cyclic polysaccharides from novel strains of *Rhizobium phaseoli*.

U.S. Pat. No. 4,535,153 to Kano et al. is directed to the production of polysaccharides by novel species of *Pseudomonas*.

The polysaccharide produced by the organism *Z. ramigera* is similar to xanthan gum. For purposes of the present invention, the polysaccharide by *Z. ramigera* 115 will be known as the zooglan polysaccharide or zooglan.

Reference is made to U.S. Pat. 4,851,393 to Rha et al. for a description of *Zoogloea ramigera*, which describes the microorganism as a Gram-negative, rod-shaped, floc-forming, single polar flagellated, obligate aerobe found in aerobic waste treatment facilities and natural aquatic habitats, which can be grown on a variety of carbon and nitrogen sources. It is distinguished from other Gram-negative Pseudomonads by the presence of an exocellular polymer which is believed to cause flocculation and occurs, in some strains, such as *Z. ramigera* 115, as a zoogloeal or capsule-like matrix. Reference is also made to UK Patent Application GB 2139 638A to Molin, N. L. et al., PCT patent no. W088/00948 to Sinskey, A. J. et al., PCT patent no. 89/09270 to Easson D. D. et al., and Norberg, A. B., 1984, *Biotech. and Bioeng.*, Vol. 26, pgs. 239–246, and Norberg, A. and S. Rydin, 1983, *Biotech. and Bioeng.*, Vol. 26, pgs. 265–268, for a further description of *Zoogloea ramigera*.

Easson et al. (supra.) and Sinskey et al. (supra.) are directed to methods of producing polysaccharides having altered functional groups. The methods disclosed provide polysaccharides having modified surface charge due to variations in the charged moieties on the polysaccharide which, unlike the present invention, are the result of alteration of the genetic structure of the organisms rather than the environment in which the organism is grown and the gum is harvested.

The polysaccharide produced by *Z. ramigera* has similar functions to other biopolymers in the industry, such as water binding capacity, moisturizing effect, thickening, lubrication, adhesion. Additionally, the polysaccharide produced by *Zoogloea ramigera* has the ability to bind transition and heavy metal ions (Dugan, P. R., 1975, *Environ. Prot. Tech.*, Report No. EPA-600/2-75-032). However, these zooglan polysaccharides have been treated like other capsular or zoogloeal polysaccharides in that they are processed in an alkali environment to remove the polysaccharide from the organism. The alkali environment is also effective in removing succinyl moieties from the zooglan polysaccharide.

While zooglan polysaccharides are known to have certain functional properties similar to other polysaccharides, such as those listed above, the characteristic functions of prior art zooglan polysaccharides have been somewhat limited in scope. This is presumably due to the inherent structure of the prior art zooglan polysaccharides or to the prior art methods of zooglan polysaccharide production.

SUMMARY OF THE INVENTION

It is therefore an object of the present invention to produce a zooglan polysaccharide with superior properties than previously reported.

It is another object of the present invention to produce a zooglan polysaccharide which will exhibit better thickening and metal chelating properties in commercial applications.

It is another object of the present invention to produce a novel zooglan polysaccharide from a microorganism which can be cultured in whey.

It is still further an object of the present invention to produce a novel zooglan polysaccharide which will provide improved color and optical clarity in solution.

It is further an object of the present invention to produce a novel succinylated zooglan polysaccharide.

These objects and others are addressed by the present invention which is directed to a zooglan polysaccharide composition, which is primarily a carbohydrate, wherein the carbohydrate is bound with succinate.

The present invention is also directed to a process for the production of a succinylated zooglan polysaccharide comprising incubating the organism Z. ramigera in a fermentation medium containing a carbon source, a nitrogen source, trace inorganic elements and vitamins, at a temperature and Ph sufficient to recover an anionic succinylated zooglan polysaccharide in recoverable quantities, and recovering an anionic succinylated zooglan polysaccharide in the presence of a quantity of a succinate lysing agent sufficient to leave the succinylated zooglan polysaccharide with a predetermined percentage of succinate on the zooglan polysaccharide.

The present invention is also directed to a process for removing metal cations from an aqueous medium comprising adding a recoverable succinylated zooglan polysaccharide in combination with a cationic matrix to support the zooglan polysaccharide to the aqueous medium in a sufficient amount to bind the metal cation to form a polysaccharide metal cation precipitate, removing the polysaccharide metal cation precipitate from the aqueous medium, and recovering the succinylated zooglan polysaccharide for reuse.

The present invention is also directed to an anionic succinylated zooglan polysaccharide produced by the process described in the previous paragraph.

The present invention is further directed to a succinylated zooglan polysaccharide composition having a molecular weight of about $7-9 \times 10^6$, which is primarily a carbohydrate, wherein the carbohydrate is bound with succinate in an amount from about 0.05 to 6.0% (w/w).

The present invention is also directed to a process for removing metal cations from an aqueous medium comprising adding a succinylated zooglan polysaccharide to the aqueous medium in a sufficient amount to bind the metal cation to form a polysaccharide-metal cation precipitate, wherein the succinylated zooglan polysaccharide is supported on an inert support matrix, removing the polysaccharide-metal cation precipitate from the aqueous medium, and recovering the succinylated zooglan polysaccharide from the waste metal for reuse.

The present invention is also directed to a process for forming a gel from an aqueous solution comprising adding a zooglan polysaccharide having a succinate content between about 3.0 and 6.0% (w/w) in sufficient quantity to gel the aqueous solution, and heating the solution to a sufficient temperature to gel the aqueous solution.

The properties of the novel zooglan polysaccharide of the present invention are improved due to the presence of succinate. Unlike the present invention, the generally accepted process for producing zooglan polysaccharides involved the incubation of Z. ramigera 115 in a fermentation medium followed by addition of an alkaline solution to dissociate the polysaccharide from the Z. ramigera 115 cell. Z. ramigera 115 is known to form capsules and flocculate. Alkaline solutions such as in a 0.1-0.2 N solution of sodium or ammonium hydroxide have been used to perform the dissociation. The alkali environment also removed succinyl moieties from the polysaccharide. Thus, the alkali environment is also known as a "succinate lysing agent" because of its ability to lyse or separate succinate from the polysaccharide. It has now been discovered that maintaining succinate on a polysaccharide produced by the action of Z. ramigera 115 is beneficial.

The bound succinate has the advantages of enhancing the thickening properties and metal chelating properties in a polysaccharide solution.

While some of the prior art references, notably Easson et al. (supra.) and Sinskey et al. (supra.) allege superior polysaccharide properties as a result of the genetic modification of the structure of the polysaccharide, the present invention utilizes environmental and process modifications to achieve an improved polysaccharide quality. For example, the zooglan polysaccharide of the present invention can be produced from the microorganism when the Z. ramigera is cultured in the presence of lactose, a component of whey. This provides a specific economical advantage over the production of xanthan, which cannot be economically produced on a commercial basis in a lactose or whey environment. For purposes of the present invention, the term "whey" is defined as the fluid medium containing a very low concentration of milk solids and a high concentration of lactose and is produced as a by-product in the manufacture of cheese. The term "whey" is also meant to include whole whey and reconstituted whey of up to 18% solids and ultrafiltered whey, referred to as "whey permeate".

The zooglan polysaccharide of the present invention has a wide variety of uses, both in food and in non-food industries. In food, the zooglan polysaccharide has applications as an efficient thickener and a water retention agent for the stabilization of food products. In industry, the zooglan polysaccharide is useful as a thickening, suspending, emulsifying, stabilizing, lubricating, film-forming or binding agent. Its specific uses include adhesives, pastes, building materials, cleaners and polishes, seed coatings, binders, wet-end additives and coatings for paper products, petroleum and water-well drilling muds, cosmetics, pharmaceutical suspensions and emulsions. The polysaccharide also appears to act as a lubricant based upon tactile evaluation of aqueous polysaccharide solutions.

Of primary importance to the zooglan polysaccharide of the present invention is its use in wastewater treatment. Wastewater, from sewage, factory or other waste treatment plants, may contain heavy metals. Examples of metals removed from wastewater can include cadmium, cobalt, nickel and iron. The zooglan polysaccharide of the present invention acts as a heavy metal ion removal agent for wastewater treatment. It is believed that the mechanism of ion removal involves ionic attraction of the positively charged metal to the negatively charged polysaccharide. The metal-polysaccharide complex is insoluble and falls out of the solution.

It is also significant to note that the zooglan polysaccharide of the present invention may be reusable when it is bound to a cationic support matrix, hereafter referred to as "support matrix" or simply "matrix". The zooglan polysaccharide-matrix of the present invention can be compared to a "free-floating magnet" in an aqueous medium. As the polysaccharide-matrix travels through the aqueous medium, it binds to the metal ions. The insoluble polysaccharide-matrix-metal complex may be removed from the aqueous solution by mechanical means such as centrifugation, filtration or settling. The metal complex into a concentrated waste stream by addition of acid. The insoluble polysaccharide-matrix complex may then be removed from the waste stream by mechanical methods, enabling it to be recycled for further use. The main advantage of binding the polysaccharide to an insoluble matrix is the ability to easily reuse the polysaccharide for metal recovery, thereby reducing the cost of the process. In previously-described methods for utilization of the zooglan polysaccharide for metal recovery, the polysaccharide dissolves along with the metal into the waste stream after release of the metal from the insoluble polysaccharide-metal complex (Norberg, A. B. and S. Rydin, 1984, *Biotechnol. Bioeng.*, vol. 26, pp. 239-246). Resolubilization of the polysaccharide makes it difficult to recycle the polysaccharide because it cannot be easily separated from the soluble metal.

Other objects, advantages and features of the present invention will become apparent from the following specification when taken in conjunction with the accompanying drawings.

DETAILED DESCRIPTION OF THE INVENTION

Figure 1:
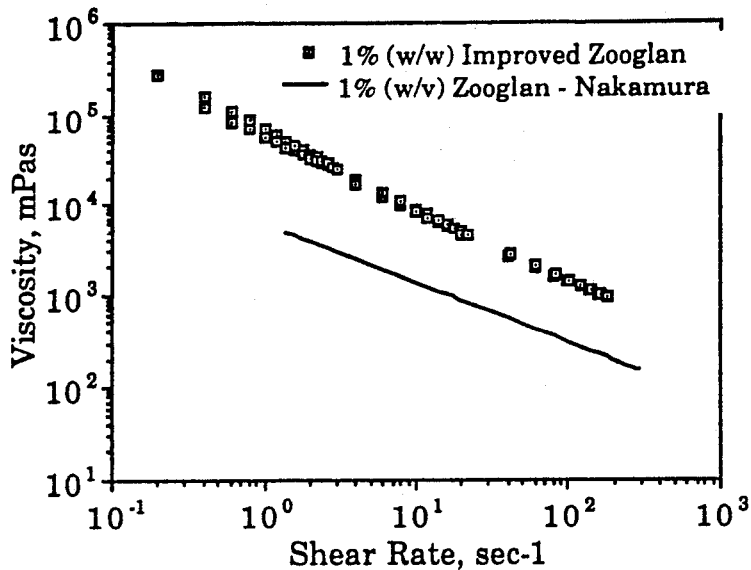
FIG. 1 is a graph illustrating a comparison of the steady shear viscosity of aqueous solutions of 1% (w/w) improved zooglan polysaccharide of the present invention and a previously reported zooglan polysaccharide, as described in Experiment 1.

The present invention is directed to a method for producing and utilizing a succinylated zooglan polysaccharide isolated from *Z. ramigera* 115. For purposes of the present invention, the term *Zoogloea ramigera, Z. ramigera* 115 or *Z. ramigera* is directed to a strain of microorganism, entitled *Zoogloea ramigera* 115, obtained from the American Type Culture Collection (ATCC), Rockville, Md., having ATCC registration number 25935. The Zoogloea ramigera 115 microorganism obtained from ATCC will hereafter be referred to as *Z. ramigera* or *Z. ramigera* 115. The zooglan polysaccharide obtained from the ATCC strain of *Z. ramigera* will hereafter be referred to as zooglan polysaccharide or zooglan.

Zooglan Polysaccharide

The zooglan polysaccharide produced by *Z. ramigera* is generally a very high molecular weight anionic polysaccharide. The carbohydrate portion of the purified polysaccharide consists of glucose and galactose in the approximate molar ratio of 2:1 based upon HPLC and 500 Mhz proton NMR analysis (Franzen, L. E. and A. B. Norberg, 1984, *Carbohyd. Res.*, 128, pp. 111-118; Easson, D. D., 1987, *A Recombinant DNA Approach to the Design and Synthesis of Novel Polysaccharides*, Sc. D. Thesis, Massachusetts Institute of Technology, Cambridge, Mass.) of the triflouroacetic acid hydrolysis products. The polysaccharide is substituted with pyruvate, in a pyruvyl ketal linkage to a carbohydrate residue, from approximately 2.5 to 3.6% (w/w). Furthermore, the improved polysaccharide is substituted with succinate, in an ester linkage to a carbohydrate residue, in varying degrees from roughly 0.05 to 6.0% (w/w). The presence of succinate in the zooglan polysaccharide results in superior properties than previously reported. The presence of succinate improves the thickening efficiency of the polysaccharide.

The practice of the present invention is enabled by the cultivation of a pure culture of *Z. ramigera* 115 under certain restricted environmental conditions. These unique environmental and process modifications achieve an improved polysaccharide quality by enabling the incorporation of high levels of succinate in the polysaccharide.

Succinate Modifier

It is believed that the presence of certain trace metals, vitamins and good oxygen transfer enables the production of the improved polysaccharide of the present invention. The presence of succinate vastly improves the thickening efficiency of the polysaccharide.

Succinate is present in the polysaccharide in amounts up to 6.0% by weight. Preferably, the amount of succinate is between 1.5 and 4.8% by weight, depending upon its use. For example, a high succinylated zooglan polysaccharide, in which succinate is present in preferred amounts between 3.0 and 5.0% by weight is useful as a thickener. Low succinylated zooglan polysaccharides, in which succinate is present in preferred amounts between 0.05 and 1.5% by weight, are useful in waste metal recovery operations.

The succinate is added as a modifying group to the polysaccharide backbone. An illustration of the structural formula is as follows:

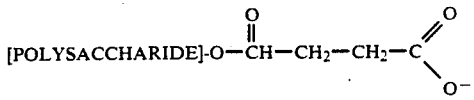

Succinate is not endemic to the zooglan polysaccharide. It is believed to only be incorporated into the polysaccharide and retained under a limited range of production and recovery conditions. The degree of succinylation is effectively controlled by a combination of proper fermentation and recovery conditions. The presence of one or more trace elements, such as calcium, iron and manganese, is believed to serve as enzyme activators or co-factors. Since the substrate for succinyl addition, succinyl-CoA, is produced in the oxygen-dependent tricarboxylate acid cycle, it is believed that good oxygen transfer is essential for producing the maximum degree of succinylation in the zooglan polysaccharide.

Characterization of Zooglan Polysaccharide

The zooglan polysaccharide was produced and purified from the fermentation broth, which will be described hereinafter under zooglan production. The polysaccharide was hydrolyzed in 1 M triflouroacetic acid for 1 hour at 121° C. in a nitrogen atmosphere.

The neutral sugars were identified by comparison with pure sugar standards using HPLC involving a cation exchange resin in the calcium or lead form. These identifications were confirmed by 500 Mhz proton NMR analysis relative to sugar standards. Pyruvate presence was quantitatively determined by an enzymatic method employing a lactate dehydrogenase enzyme. Succinate presence was quantitatively determined by comparison with a pure succinate standard using HPLC involving a cation exchange resin in the hydrogen ion form. The presence of succinate was confirmed by 500 Mhz proton NMR analysis relative to a pure succinate standard.

Properties of Succinylated Zooglan Polysaccharide

The weight-average molecular weight of the succinylated zooglan polysaccharide is estimated at $7-9 \times 10^6$ daltons, as measured by static laser light scattering (Friefelder, D., 1982, *Physical Biochemistry, Applications to Biochemistry and Molecular Biology*, Second Edition, pp. 362-491, 691-698).

Irreversibly rubbery, elastic gels can be formed from aqueous solutions of a high-succinylated zooglan polysaccharide, i.e., a zooglan polysaccharide having a succinate content between about 3.0 and 6.0% (w/w), by adding the zooglan polysaccharide in sufficient quantities to thicken the aqueous solution followed by heating of the solution. The zooglan polysaccharide is added to the aqueous solution in an amount of at least about 1.0 grams/liter at a temperature between about 90° and 150° C. for about 5 to 60 minutes. Preferably, a gel will form upon exposure of the zooglan polysaccharide to the aqueous solution at temperatures of about 121° C. for at least about 15 minutes. This property has utilities for various cooked food product applications.

Zooglan Polysaccharide Production

Carbohydrate Source

A monosaccharide, disaccharide, oligosaccharide or mixture thereof can be used as the carbohydrate source in the fermentation medium. For example, suitable carbon sources can include glucose, fructose, maltose, sucrose, xylose, mannitol, lactose or the like. Lactose is the preferred carbohydrate source. The quantity of carbohydrate source in the medium depends in part on the ingredients in the medium. Generally, the amount of carbohydrate in the medium varies between 2.0% and 6.0% by weight of the medium. Additionally, it is within the scope of the present invention to utilize all carbohydrate sources which *Z. ramigera* is known to use. Examples of such sources may be found in Unz, R. F. (1984), *Bergey's Manual of Systematic Bacteriology*, p. 219.

Nitrogen Source

The nitrogen sources can be conventional, such as nitrates, ammonium salts, or amino acids. The nitrogen source can be a complex mixture of compounds, as is present in whey. Additionally, gaseous ammonia may be used as the source, and may be preferable for practical and economic reasons.

Trace Elements and Vitamins

Inorganic salts, vitamins and other ingredients, which are essential for the proper growth of the microorganism, are also added to the medium in a manner known to the art. The ingredients are those customary to trade and include, without limitation, sodium, potassium, ammonium, calcium, phosphate, sulfate, chloride, carbonate and like ions. Also included may be trace metals, such as cobalt, manganese, iron and magnesium.

General Fermentation Process

The fermentation is carried out at temperatures ranging from about 20° C. to 32° C., preferably 24° C.-27° C. Higher or lower temperatures may be possible. The pH of the nutrient medium for growing the culture and producing the zooglan polysaccharide can vary from 5 to 8, with a preferred Ph of 7.

The fermentation process requires a carbon-to-nitrogen (C/N) ratio between about 6:1 and 60:1, preferably about 20:1 and 50:1, and most preferably a ratio of 40:1 (w/w).

The level of yeast extract in the lactose defined medium required is between about 0.01 grams per liter (g/l) and 5 g/l, preferably about 1.8 g/l.

The fermentation can be carried out as either a batch or continuous process under submerged conditions in a suitable fermenter. It is within the scope of the present invention to scale up the fermentation process to industrial conditions or to scale down the process to experimental conditions according to steps known to the art.

Recovery Method

The process used to recover the polysaccharide from the fermentation broth must avoid the use of alkali treatment to prevent hydrolysis of the succinate.

*Z. ramigera* 115 cells optionally can be recovered by first removing them from the diluted fermentation broth (1 volume of broth diluted with three volumes of water) by high speed centrifugation at 40,000 to 48,000×g at least 50 minutes at temperatures from 4° C. to 25° C. The polysaccharide can be recovered from the supernatant by addition of sufficient quantities of a short-chain aliphatic alcohol such as ethanol, n-propanol or isopropanol. The addition of sufficient ethanol to achieve a 60 to 70% (v/v) solution of ethanol and broth is the preferred method for crude recovery of the polysaccharide. The addition of larger quantities of alcohol, especially isopropanol and n-propanol, may cause significant and undesirable co-precipitation of salts and polysaccharide.

The precipitate can then be harvested from the alcohol solution by decantation, filtration or centrifugation. The precipitate is then dried and milled to achieve the desired polysaccharide texture and solubilization properties. The precipitate may optionally be deionized by redissolving in water to achieve an approximate polysaccharide concentration of 1% (w/w). Small volumes of polysaccharide solutions are dialyzed against deionized water in macroporous, cellulosic tubing (molecular weight cut of approximately 10,000 daltons) to remove low molecular weight solutes for a minimum of 48 hours. The dialyzing water is changed daily. Large volumes of solution can be ultrafiltered at a constant concentration which is maintained by the cumulative addition of 5 volumes of deionized water. The solutions are then concentrated to final concentration of 5-8 g/l by ultrafiltration. A Millipore Pellicon tangential-flow plate system fitted with a 0.5 ft$^2$ 100,000 MWCO PTHK, polysulfone-type filter (Millipore Corporation, Bedford, MA) is used in the ultrafiltration step. The polysaccharide may be then precipitated, dried and milled as described previously.

Method of Production of a Useful Zooglan Polysaccharide

A zooglan polysaccharide containing 4.8% (w/w) succinate can be produced by aerobic fermentation of the *Z. ramigera* microorganism at an agitation speed of 800 rpm in a 5 liter vessel and a high rate of air sparging (roughly one volume of air per volume of broth per minute) in a medium containing a high carbon to nitrogen ratio, trace metals and salts, and vitamins which are supplied by yeast extract (or the equivalent). Reference is made to Table 1 for a preferred fermentation medium:

TABLE 1

Preferred Medium for Fermentation of the New Strain

| Component | Concentration (g/L) |
| --- | --- |
| Glucose | 45.00 |
| $(NH_4)_2SO_4$ | 1.46 |
| $KH_2PO_4$ | 1.80 |
| $K_2HPO_4$ | 3.60 |
| $MgSO_4.7H_2O$ | 0.60 |
| $CaCl_2.2H_2O$ | 0.04 |
| $FeSO_4.7H_2O$ | 0.0019 |
| $CoCl_2.6H_2O$ | 0.001 |
| $ZnSO_4.7H_2O$ | 0.001 |
| $CuSO_4.5H_2O$ | 0.001 |
| $MnSO_4.H_2O$ | 0.001 |
| $Na_2MoO_4.2H_2O$ | 0.001 |
| Yeast Extract | 1.80 |
| NaOH | to pH 7 (roughly 0.18 g/l) |

The carbon to nitrogen ratio in the preferred method of production is approximately 40 to 1 M C/N ratio. The pH is held at 7 and the temperature at 26° C.

The overall results indicate that the polysaccharide can be produced with a good yield, i.e., 0.4 g/g, and volumetric productivity, i.e., 0.3 g/l hr for a 70 hour fermentation.

Polysaccharide Produced from a Mutagenized Strain of *Z. ramigera* 115

The purity and optical clarity properties of the polysaccharide may further be improved by cultivation of a mutagenized strain of *Z. ramigera* which is unable to make its normal yellow pigment. A strain of *Z. ramigera* 115 has been isolated following nitrosoguanidine (NTG) mutagenesis (Gerhardt, P., 1981, Manual of Methods for General Bacteriology) whose morphological coloring has been altered. The ability of this strain to produce yellow pigment has been lost. As a result, such a strain imparts a white coloring to fermentation broths, as opposed to a yellow coloring imparted by the wildtype strain of *Z. ramigera* 115. Such altered strains of *Z. ramigera* 115 are preferred since their polysaccharides will not impart any yellow coloring to products or processes that utilize such polysaccharide.

A zooglan polysaccharide with a low succinate content, i.e., a succinate content between about 0.05 and 1.5% (w/w), may also be achieved by cultivation of a mutagenized strain of *Z. ramigera* 115 which produced a low-succinate zooglan polysaccharide in a non-capsular form. The strain of *Z. ramigera* 115 was also isolated following NTG mutagenesis (Gerhardt, P., 1981, supra.) by looking for colonies unable to bind the polysaccharide in a capsule. The low-succinate zooglan polysaccharide produced by this mutagenized form of *Z. ramigera* 115 is useful in waste metal recovery operations, as described in the following section.

Waste Metal Recovery Using Succinylated Zooglan Polysaccharides

Zooglan polysaccharides, which possess a lower level of succinate, i.e., 0.05% -1.5% (w/w), can be produced from NTG-mutagenized strains of *Z. ramigera* 115 and demonstrate an inability to form capsules and flocculate as described in the previous section. Such zooglan polysaccharides also thicken less efficiently than the polysaccharide from wildtype *Z. ramigera* 115. Low level succinate zooglan polysaccharides have higher polysaccharide productivities than polysaccharides produced from other cell strains as a result of these factors: 1) increased mass transfer and improved mixing in the fermentation broth resulting from lower fermentation broth viscosities; and 2) the lack of capsules and cell flocs that offer undue mass transfer resistance. Low level succinate zooglan polysaccharides are therefore preferred for the modification of food or non-food aqueous solutions, which do not require a high degree of thickening. For example, low level succinate polysaccharide can be used for the binding of metals in a metal recovering process. Low level succinate polysaccharide will be less viscous than high level succinate polysaccharide allowing greater ease of handling, such as in pumping and mixing, in all stages of the process where the polysaccharide is free of metal, i.e., not in the form of a metal-polysaccharide precipitate.

Both low and high succinylated zooglan polysaccharides have been demonstrated to be effective metal recovery agents. The cost-effectiveness of zooglan polysaccharides as metal recovery agents can be greatly improved through the use of a cationic matrix to support the polysaccharide. Currently, it is difficult to recycle zooglan in a metal recovery application: the zooglan can bind metal, but it is difficult to re-use because dissociation of the metal-zooglan complex resolubilizes both the metal ion and the zooglan. Thus, one has not achieved a separation of the metal ion from the aqueous solution. One can realistically achieve only a single use of the zooglan polysaccharide.

The binding of the support matrix to the zooglan polysaccharide prior to binding of metal ions enables the use of a more cost-effective, continuous process for metal recovery. The complex of zooglan and matrix is insoluble in aqueous solution, but still effective for metal recovery. Thus, metal ions can be removed from aqueous solution by the zooglan-matrix complex at a high pH. The zooglan-matrix-metal complex can then be separated from the aqueous stream. The metal ions may be released from the complex into a concentrated waste stream by lowering the pH. Finally, the insoluble zooglan-support may be recycled to a wastewater stream for removal of additional metal ions.

The cationic support matrix is most generally described as an inert, water insoluble material, usually in the form of a microparticle or membrane, which is covalently linked to cationic residues, such as a tertiary or quaternary amines, which have a positive charge at a pH between about 5 and 7. Examples of these materials are various cationic exchange resins, such as DOWEX (Dow Chemical, Midland, Mich.) Amerlite, Amberlyst or Biocryl (Rhom & Haas, Philadelphia, Pa.) resins. The support may be porous or non-porous. The resins are available in a range of sizes, generally greater than 0.1 cm in diameter or thickness.

The following non-limitative experiments are designed to illustrate the present invention.

EXPERIMENT 1

Steady Shear Viscosities of 1% and 0.5% Aqueous Solutions of Improved Zooglan Polysaccharide Experiment 1 was designed to compare the steady shear viscosities of 1% and 0.5% aqueous solutions of the improved zooglan polysaccharide of the present invention relative to previously published reports for zooglan polysaccharides. Aqueous zooglan polysaccharide solutions were prepared by dissolving specified amounts, i.e., 1% and 0.5% (w/w) of purified zooglan polysaccharide in distilled, deionized water and tested across a variety of shear rates and pH 7, 25° C. and no added salt. The purified zooglan polysaccharide was produced by the aerobic fermentation of the $Z.$ $ramigera$ microorganism using fast agitation (800 rpm in a 5 liter vessel) and a high rate of air sparging (roughly 1 volume air per volume broth per minute) in a medium containing a high carbon-to-nitrogen ratio, trace metals and salts, and vitamins which are supplied by the yeast extract (or equivalent). The preferred medium has been previously described in Table 1. The carbon-to-nitrogen ratio is very high, roughly 40:1 (w/w) C/N ratio.

Figure 2:
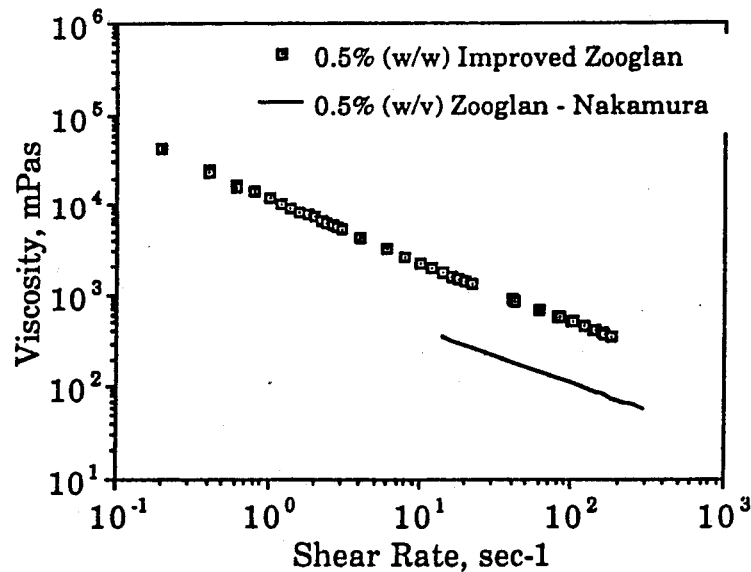
FIG. 2 is a graph illustrating a comparison of the steady shear viscosities of aqueous solutions of 0.5% (w/w) improved zooglan polysaccharide of the present invention and a previously reported zooglan polysaccharide, as described in Experiment 1.

Referring now to FIGS. 1 and 2, the results indicate that the improved, succinylated zooglan is a highly efficient thickener, being significantly more efficient than zooglan polysaccharides report by previous workers (Nakamura, T. et al., 1987, *Flocculation in Biotechnology and Separation Systems*, Y. A. Attia, ed., pp. 399–413; and U.S. Pat. No. 4,851,393 to Rha et al.). Referring now to FIG. 1, it can be seen that for equal concentrations of 1% polysaccharide, the improved zooglan polysaccharide builds roughly an order of magnitude higher viscosity than the original zooglan. In other words, one would require only one-half the amount of improved zooglan to impart the same aqueous solution viscosity provided by the original zooglan. This result is supported in studies with equal concentrations of 0.5% polysaccharide, as illustrated in FIG. 2.

EXPERIMENT 2

Comparison of Steady Shear Viscosity Of Zooglan Polysaccharide of the Present Invention to Xanthan Gum Experiment 2 was designed to compare the steady shear viscosity of a 1% (w/w) solution and a 0.5% (w/w) solution of xanthan gum and the improved zooglan polysaccharide. Reference is made to Experiment 1 for a description of the procedure.

Figure 3:
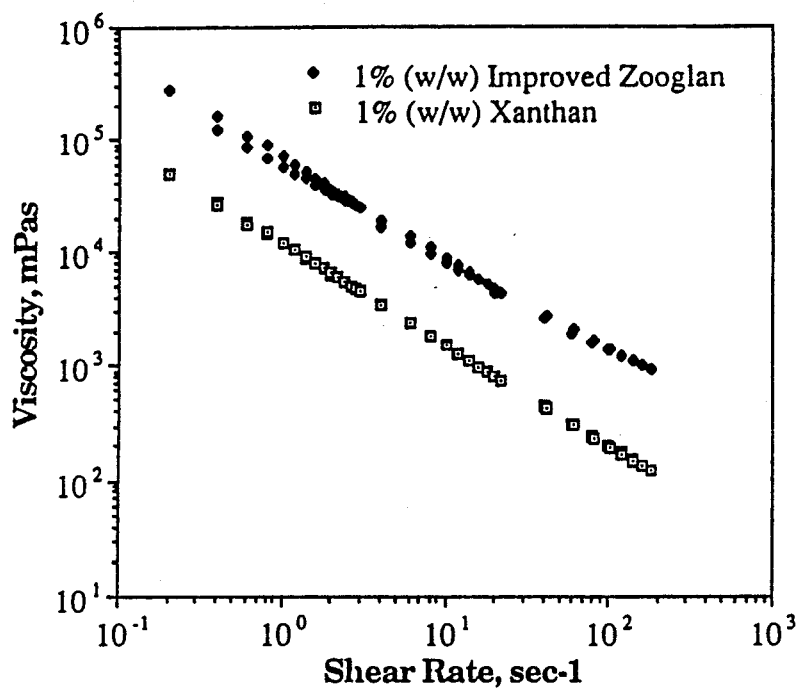
FIG. 3 is a graph illustrating a comparison of steady shear viscosities of 1% (w/w) solutions of xanthan gum and the improved zooglan polysaccharide, as described in Experiment 2.
Figure 4:
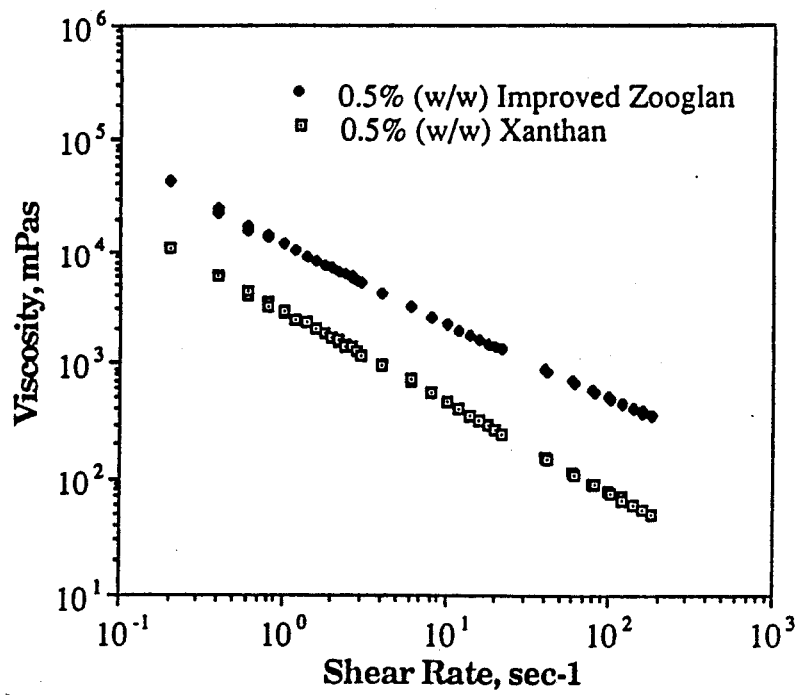
FIG. 4 is a graph illustrating a comparison of the steady shear viscosity of 0.5% (w/w) solution of xanthan gum and the improved zooglan polysaccharide gum, as described in Experiment 2.

Referring now to FIGS. 3 and 4, it can be seen that the improved zooglan polysaccharide provides significantly better thickening efficiency than the leading microbial polysaccharide, xanthan gum (Aldrich Chemical, Milwaukee, Wis.).

EXPERIMENT 3

Steady Shear Viscosity of Aqueous Zooglan Polysaccharide Solutions Across a Range of pH Experiment 3 was designed to compare the steady shear viscosity of aqueous zooglan polysaccharide solutions across a range of pH. Reference is made to Experiment 1 for a description of the procedure. Aqueous polysaccharide solutions of specified pH were prepared by addition of varying amounts of 4N hydrochloric acid or 4N sodium hydroxide to a 1% (w/w) purified polysaccharide solution.

Figure 5:
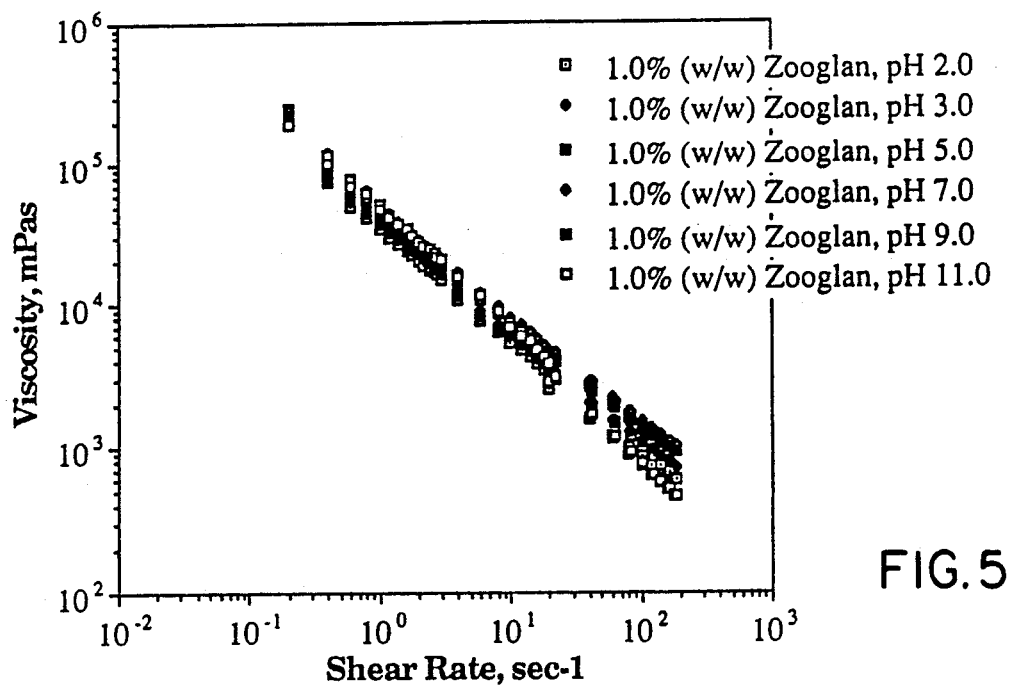
FIG. 5 is a graph illustrating the viscosity versus shear rate for a 1% (w/w) zooglan polysaccharide solution at various pH's (2-11), as described in Experiment 3.
Figure 6:
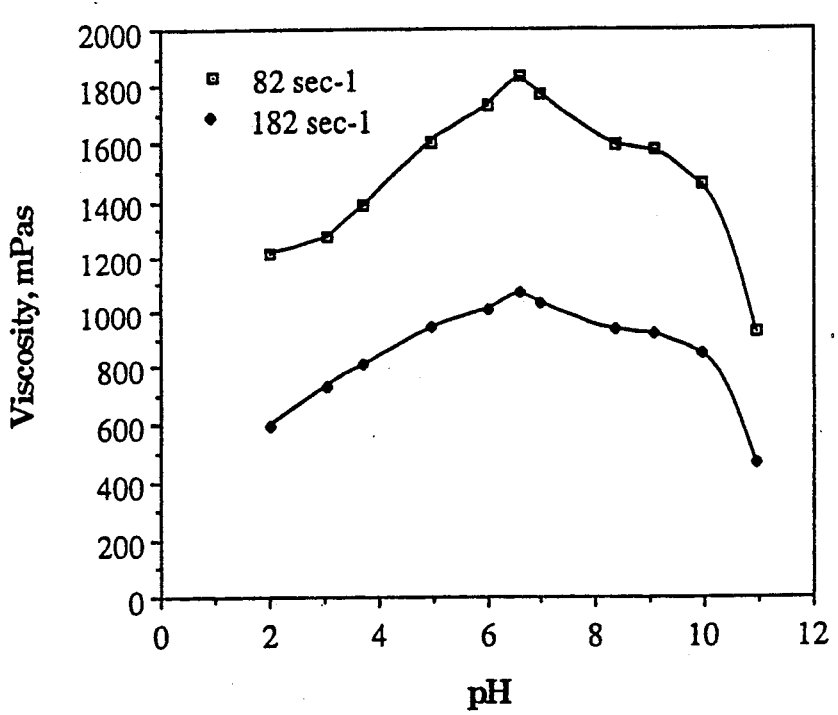
FIG. 6 is a graph illustrating the comparison of the viscosity versus Ph for a 1% (w/w) zooglan polysaccharide solution at various shear rates, as described in Experiment 3..

The steady shear viscosity across a range of pH is illustrated in FIGS. 5 and 6. These results indicate that the thickening properties of the zooglan polysaccharide are very stable from pH 2 to 11, decreasing only slightly at the extremes of this pH range. Thus, consistent thickening results can be achieved in a broad range of food and non-food formulations, even as the pH of the system may change with aging.

EXPERIMENT 4

Steady Shear Viscosity of Aqueous Zooglan Polysaccharide Solutions as a Function of Potassium Chloride (KCl), Calcium Chloride ($CaCl_2$) and Magnesium Chloride ($MgCl_2$) Salt Aqueous polysaccharide solutions of specified salt concentrations were prepared by adding varying amounts of 2M salt solutions to a 1% (w/w) purified polysaccharide solution. Sufficient distilled, deionized water was added to bring the final polysaccharide of each solution to 0.5% (w/w).

Figure 7:
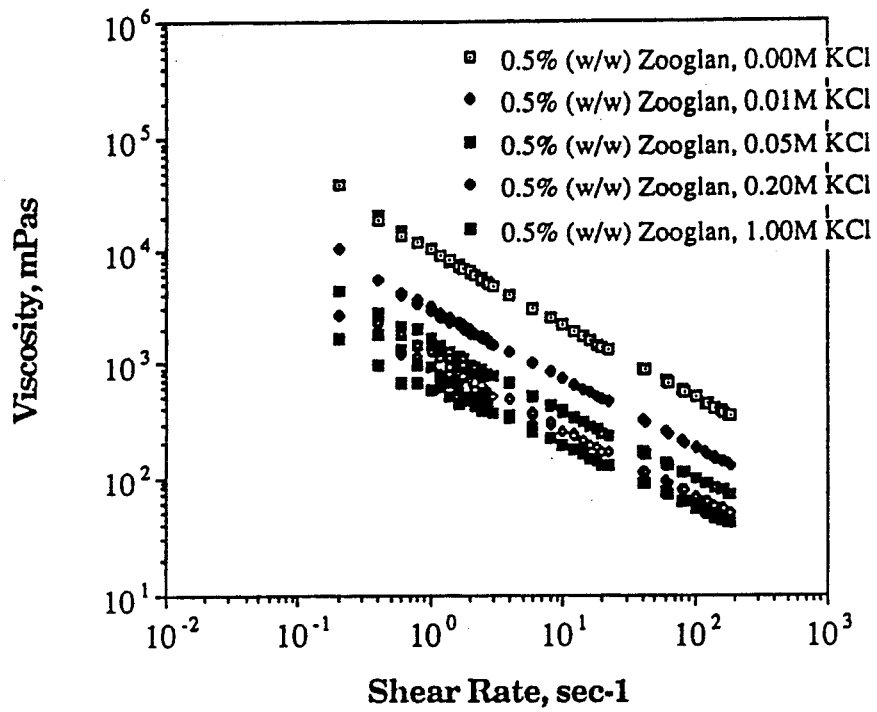
FIG. 7 is a graph illustrating the steady shear viscosity of aqueous polysaccharide solutions as a function of potassium chloride concentration, as described in Experiment 4.
Figure 8:
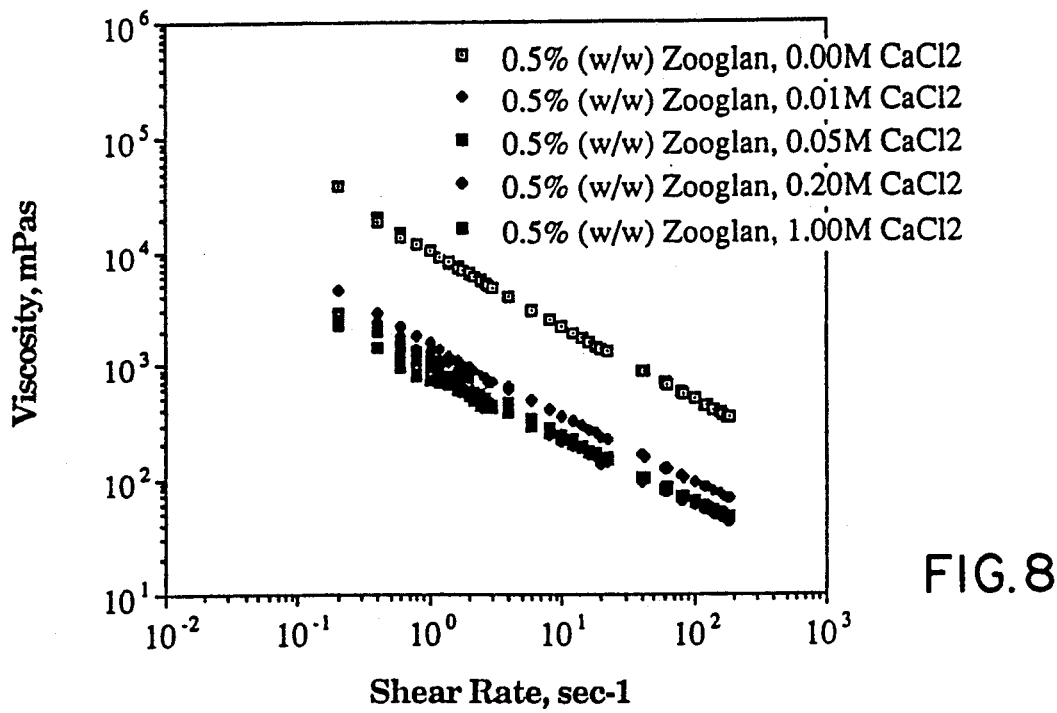
FIG. 8 is graph illustrating the steady shear viscosity of aqueous polysaccharide solutions as a function of calcium chloride concentration, as described in Experiment 4.
Figure 9:
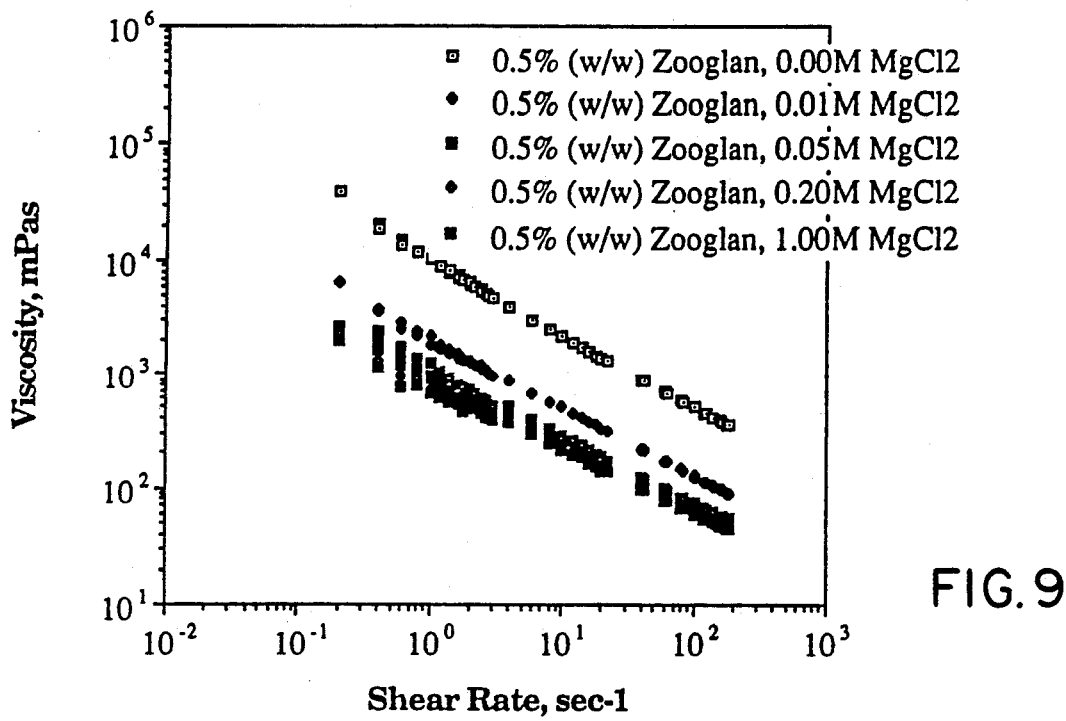
FIG. 9 is a graph illustrating the steady shear viscosity of aqueous polysaccharide solutions as a function of magnesium chloride concentration, as described in Experiment 4.

The steady shear viscosity of aqueous zooglan polysaccharide solutions as a function of potassium chloride, calcium chloride and magnesium chloride is illustrated in FIGS. 7–9. These results indicate that the succinylated polysaccharide remains soluble and builds viscosity in systems containing high levels of most monovalent and divalent salts. It is important to note, however, that viscosity generally tends to decrease as the level of salt increases, being more noticeable at lower shear rates and less noticeable at higher shear rates.

EXPERIMENT 5

Steady Shear Viscosity of Aqueous Solutions Of Zooglan Polysaccharide as a Result of Varying Degrees of Succinylation Experiment 5 was designed to study the steady shear viscosity of aqueous solutions of improved zooglan polysaccharides of the present invention as a function of the degree of succinylation of the zooglan polysaccharide. The compositions of five zooglan polysaccharides which exhibited different steady shear viscosities were studied by HPLC and enzymatic assay. Four of the polysaccharides were produced from wildtype $Z.$ $ramigera$ fermentation of lactose or glucose defined medium, or whey permeate, while the other polysaccharide was produced from capsule-deficient mutant of $Z.$ $ramigera$ fermentation of lactose defined medium, i.e., the medium of Table 1 (supra.) in which glucose is replaced by lactose monohydrate. 500 MHz proton NMR spectra were obtained for three of the polysaccharides to confirm the quantitative analysis by HPLC. The five polysaccharides are designated as follows in all future discussion: (zoo-glc) zooglan produced from wildtype $Z.$ $ramigera$ fermentation of glucose; (zoo-lac)

zooglan produced from wildtype Z. ramigera fermentation of lactose; (zoo-cap) zooglan produced from capsule-deficient mutant of Z. ramigera fermentation of lactose; (zoo-wp1) zooglan produced from wildtype Z. ramigera 115 fermentation on whey permeate; and (zoo-wp2) zooglan produced from wildtype Z. ramigera 115 fermentation on whey permeate.

Figure 10:
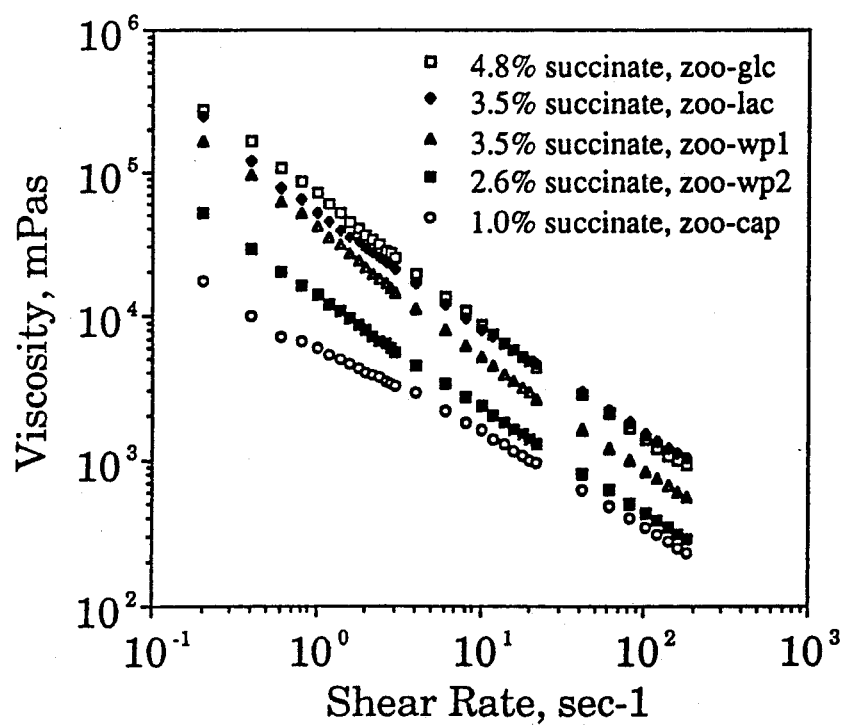
FIG. 10 is a graph illustrating a comparison of the steady shear viscosities of 1% (w/w) aqueous solutions of zooglan polysaccharides with varying levels of succinate, as described in Experiment 5.

The effect of the degree of succinylation upon the steady shear viscosities of aqueous zooglan solutions is illustrated in FIG. 10. Referring to FIG. 10, it can be seen that the steady shear viscosity, especially at high shear rates, increases as the degree of succinylation in the zooglan polysaccharide increases.

Zoo-glc and zoo-cap polysaccharides exhibited the largest difference in steady shear viscosity. For example, the steady shear viscosity at 100 sec$^{-1}$ of the zoo-glc polysaccharide was 8800 mPa·s versus 1590 mPa·s obtained for the zoo-cap polysaccharide.

A comparison of the H$^+$ cation exchange HPLC chromatograms indicated that the major difference in the composition of these polysaccharides was the level of succinate, as illustrated on FIG. 10. The succinate levels varied from 1.0% to 4.8% (w/w) for the three polysaccharides. Glucose and galactose were found in the approximate molar ratio of 2:1, while pyruvate was present at 3.3 to 3.5% (w/w).

EXPERIMENT 6

Improved Productive of Low Level Succinate Mutant Over Wildtype Z. ramigera 115

Experiment 6 was designed to determine the polysaccharide productivity of a low level succinate mutant of Z. ramigera 115 in comparison to the wildtype strain. Each strain was tested by individual fermentation using the fermentation conditions and medium described in Experiment 1. Table 2 describes the results that were obtained:

TABLE 2

Results of a 30 hour Fermentation

| Strain | Polysaccharide Productivity (g/L/hr) | Polysaccharide Yield on Carbon Source (g/g) |
|---|---|---|
| Wildtype | 0.13 | 0.09 |
| Low succinate mutant | 0.30 | 0.20 |

EXPERIMENT 7

Agility of Zooglan Polysaccharide to Remove Copper Ions From Wastewater Solutions The ability of succinylated zooglan polysaccharide to remove hazardous metals from aqueous solutions was evaluated using copper-containing solutions as the example system. Copper sulfate solutions containing 3 mM, 8 mM, and 16mM, Cu$^{++}$ were prepared by dissolving CuSO$_4$.5H$_2$O(Mallinckrodt, Paris, Ky.) in deionized, distilled water. 15 ml of a 0.1% (w/v), pH 3.5 solution of zooglan polysaccharide (high decree of succinylation or low decree of succinylation) were added to 15 ml of copper sulfate solution while continuously stirring. The pH of the clear solution was raised to 5.5 by the addition of an appropriate volume of 4N NaOH, Extensive precipitation was observed at pH>4.7. The solution was equilibrated at pH 5.5 for 15 minutes. The precipitate was pelleted by centrifugation at 18,000×g and 25° C. for 10 minutes. The clear supernatant was decanted from the precipitant and was analyzed for copper content along with initial samples. Copper ion concentration was determined by inductively coupled emission spectroscopy. The total copper absorbed by the polysaccharide was then determined by a mass balance.

Figure 11:
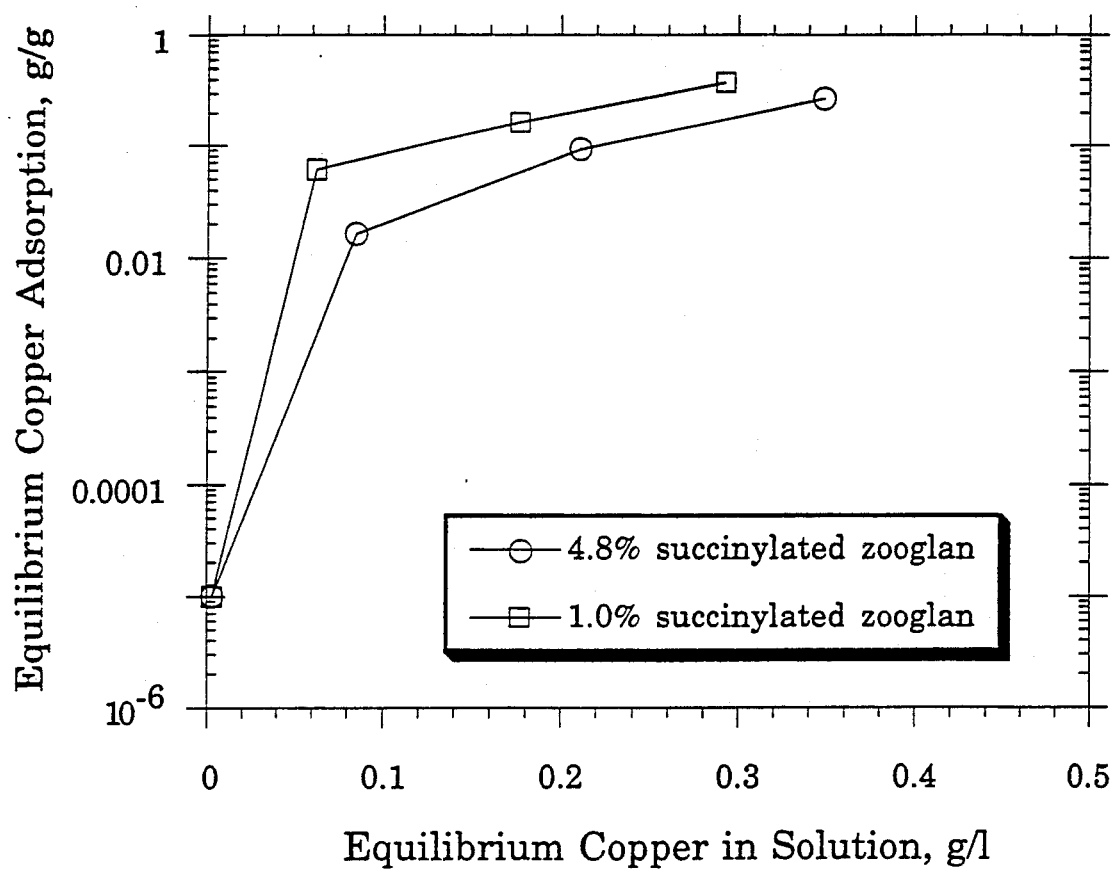
FIG. 11 is a graph illustrating the effect of the zooglan polysaccharide of the present invention on removal of copper from a wastewater solution, as described in Experiment 7.

Reference is made to the following Table 3 and FIG. 11 for an illustration of the results of this experiment.

TABLE 3

Copper Adsorption by Zooglan Polysaccharide

| Maximum Copper Adsorption g Cu$^{++}$/g gum) | Initial [Copper] (g/l) | Type of Zooglan |
|---|---|---|
| 0.38 | 0.49 | Low[1] |
| 0.27 | 0.49 | High[2] |
| 0.060 | 0.09 | Low |
| 0.016 | 0.09 | High |

[1]Low-succinylated zooglan polysaccharide
[2]High-succinylated zooglan polysaccharide Referring now to Table 3, it can be seen that the improved zooglan polysaccharide was very effective at removing copper present in high and low concentrations. Normally, the amount of metal adsorbed would increase as the metal concentration increases until it reaches a limiting value, i.e., the maximum capacity of the adsorbent. It is apparent that the metal-binding capacity of the low-succinylated zooglan is equal to or better than the metal-binding capacity of the high-succinylated zooglan. This advantage, coupled with the ease of processing, i.e., pumping, mixing and settling, indicates that low succinylated polysaccharides are preferred for metal recovery applications.

Based upon this study, it is believed that the degree of succinylation can be most effectively controlled by the combination of proper fermentation and recovery conditions. In particular, it is believed that the presence of several trace metals such as calcium, iron and manganese, which may serve as enzyme activators or cofactors, and good oxygen transfer are essential for producing the maximum degree of succinylation. The recovery process must not subject the polysaccharide to strong base or acid environments to prevent hydrolysis of the succinate residue from the polysaccharide chain. Succinyl and acyl monoester linkages to carbohydrates are particularly alkali labile. Limited acid/base treatment, however, may be an effective method for controlling the degree of succinylation; hence enabling the producer to tailor the properties of the polysaccharide to suit the needs of a particular customer.

EXPERIMENT 8

Manipulation of Succinate Content on Zooglan Polysaccharide by Deliberate Exposure to Succinate Lysing Agent The effect of alkali exposure on cleavage of succinate from the succinylated zooglan polysaccharide was investigated by treating purified polysaccharide containing 4.8% succinate with specified levels of sodium hydroxide for various lengths of time. Dilute 1% (w/w) aqueous solutions of succinylated zooglan polysaccharide were combined with small quantities to a 1N NaOH solution to achieve a final sodium hydroxide concentration of 0.1 or 0.25 NaOH for either 10 or 30 minutes. After exposure, the solution was immediately precipitated with 3 volumes of ethanol. The precipitate was recovered by centrifugation and redissolved in deionized water. This solution was dialyzed for two days, lyophilized and finally hydrolyzed according to standard procedures known to the art. The succinate content of the polysaccharides was quantified by HPLC. Reference is made to the following Table 4 for the results of this experiment:

TABLE 4

Effect of Alkali Exposure on Succinate Content of 4.8% Succinylated Zooglan Polysaccharide

| Treatment | % Reduction in Succinate Content from Initial Value of 4.8%[1] |
|---|---|
| Control - pH 7, no added alkali | 2.3 |
| 0.10N NaOH, 30 minutes | 90.8 |
| 0.25N NaOH, 10 minutes | >97.1[2] |
| 0.25N NaOH, 30 minutes | >99.9 |

[1]Average value of two independent measurements
[2]A value expressed as ">" result indicates a value below the limit of detectability.

It is believed that use of a low level succinate mutant will always be inherently better than the wildtype strain in terms of product productivity and yield as a result of a lower broth viscosity imparted by the gum of the low level succinate mutant in comparison to the gum from wildtype Z. ramigera 115.

Thus, it can be seen that all of the properties of the zooglan polysaccharide of the present invention indicate that the polysaccharide can efficiently modify the rheology of a wide range of aqueous systems, making it useful in both food and non-food applications.

It is understood that the invention is not confined to the particular construction and arrangement herein described, but embraces such modified forms thereof as come within the following claims.

What is claimed:

1. An anionic succinylated zooglan polysaccharide produced by the process comprising:
    a) incubating the organism Zoogloea ramigera 115 (ATCC 25935) in a fermentation medium containing a carbon source, a nitrogen source, wherein the ratio of carbon to nitrogen ratio is at a range of 60:1 to 10:1, trace inorganic elements and vitamins, at a temperature of 20° C.-32° C. and pH of 5-8; and
    b) recovering an anionic succinylated zooglan polysaccharide in the presence of a quantity of a succinate lysing agent sufficient to leave the succinylated zooglan polysaccharide with a predetermined percentage of succinate on the zooglan polysaccharide.

2. The zooglan polysaccharide of claim 1 which is substituted with the pyruvate such that the amount of pyruvate in the polysaccharide is between about 2.5% and 3.6% (w/w).

3. The zooglan polysaccharide of claim 1 produced from the organism Zoogloea ramigera 115.

4. The zooglan polysaccharide of claim 3 wherein the organis Zoogloea ramigera 115 is a mutagenized strain which is unable to make a normal yellow pigment characteristic of Zoogloea ramigera 115.

5. The zooglan polysaccharide of claim 1 wherein the anionic succinylated zooglan polysaccharide is recovered in the absence of a succinate lysing agent.

6. The zooglan polysaccharide of claim 1 wherein the succinate is present on the zooglan polysaccharide in an amount between 0.05% and 6.0% (w/w).

7. The zooglan polysaccharide of claim 1 wherein the succinate is present on the zooglan polysaccharide in an amount between 1.5% and 4.8% (w/w).

8. The zooglan polysaccharide of claim 1 wherein the succinate is present on the zooglan polysaccharide in an amount between 3.0% and 5.0% (w/w).

9. The zooglan polysaccharide of claim 1 wherein the succinate is present on the zooglan polysaccharide in an amount between 0.05% and 1.5% (w/w).

10. The zooglan polysaccharide of claim 1 wherein the organism is incubated in an aerobic fermenter.

11. The zooglan polysaccharide of claim 1 wherein the carbon to nitrogen ratio is 40:1.

12. The zooglan polysaccharide of claim 1 wherein the pH is 7 and the temperature is 26° C.

13. The zooglan polysaccharide of claim 1 wherein the carbon source is selected from the group consisting of glucose, fructose, maltose, sucrose, xylose, mannitol and lactose.

14. The zooglan polysaccharide of claim 1 wherein the carbon source if lactose.

15. The zooglan polysaccharide of claim 1 wherein the carbon source is sucrose.

16. The zooglan polysaccharide of claim 1 wherein the fermentation medium contains whey or whey permeate.

17. The zooglan polysaccharide of claim 1 wherein the organism Zoogloea ramigera 115 is a mutagenized strain which is unable to make a normal yellow pigment characteristic of Zoogloea ramigera 115.

18. The zooglan polysaccharide of claim 17 wherein the mutagenized strain of Zoogloea ramigera 115 was isolated following nitrosuguanidine mutagenesis.

19. The zooglan polysaccharide of claim 1 wherein the organism Zoogloea ramigera 115 is a mutagenized strain which produces a zooglan polysaccharide with a succinate content between about 0.05 and 1.5% (w/w).

20. A zooglan polysaccharide composition containing a zooglan polysaccharide having a molecular weight of about $7-9 \times 10^6$, wherein the zooglan polysaccharide is primarily a carbohydrate, wherein the carbohydrate is bound with succinate in an amount from about 1.5 to 6.0% (w/w) and a dilute carrier.

* * * * *

UNITED STATES PATENT AND TRADEMARK OFFICE
CERTIFICATE OF CORRECTION

PATENT NO. : 5,118,803
DATED : June 2, 1992
INVENTOR(S) : James H. Flatt, Timothy A. Cooper It is certified that error appears in the above-indentified patent and that said Letters Patent is hereby corrected as shown below:

Column 1, line 61, "Kano" should read --Kang--.

Column 3, line 60, "in a" should read --a--.

Column 4, line 63, "The metal" should read --The metal may be released from the polysaccharide-matrix-metal--.

Column 9, line 1, "cut of" should read --cutoff--.

Column 11, line 60, "i%" should read --1%--.

Column 13, line 29, "Productive" should read --Productivity--.

Column 13, line 50, "Agility" should read --Ability--.

Column 13, line 57, "$CuSO_4.5H_2O$" should read --$CuSO_4 \cdot 5H_2O$--.

Column 15, line 53, "claim 1" should read --claim 20--.

Column 16, line 2, "organis" should read --organism--.

Column 16, line 31, "if" should read --is--.

Signed and Sealed this

Seventh Day of September, 1993

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,118,803
DATED : June 2, 1992
INVENTOR(S) : James H. Flatt and Timothy A. Cooper It is certified that error appears in the above-indentified patent and that said Letters Patent is hereby corrected as shown below:

Column 3, line 8, "Ph" should read --pH--.

Column 5, line 41, "Ph" should read --pH--.

Column 8, line 27, "Ph" should read --pH--.

Signed and Sealed this

First Day of March, 1994

Attest:

BRUCE LEHMAN

Attesting Officer

Commissioner of Patents and Trademarks